United States Patent [19]
Starr et al.

[11] Patent Number: 5,517,986
[45] Date of Patent: May 21, 1996

[54] TWO-POINT/FOUR-POINT ADJUSTABLE HEADGEAR FOR GAS DELIVERY MASK

[75] Inventors: Eric W. Starr, Pittsburgh; Mary T. Walthour, Pitcairn, both of Pa.

[73] Assignee: Respironics, Inc., Murrysville, Pa.

[21] Appl. No.: 128,984

[22] Filed: Sep. 28, 1993

[51] Int. Cl.$^6$ .................... A62B 18/08; A62B 17/04; A62B 18/02
[52] U.S. Cl. .................... 128/206.24; 128/201.23; 128/205.25; 128/207.11; 128/DIG. 15; 128/206.27
[58] Field of Search .................... 128/201.22, 201.23, 128/201.28, 207.11, 207.17, 206.28, DIG. 15, DIG. 26, 206.24, 205.25, 206.27; 2/410, 417, 418, 420, 422, 9, 183, 173

[56] References Cited

U.S. PATENT DOCUMENTS

| | | | |
|---|---|---|---|
| 1,356,708 | 10/1920 | Goodyear | 128/207.11 |
| 1,443,820 | 1/1923 | Hudson | 128/207.11 |
| 1,706,601 | 3/1929 | Drager | 128/207.11 |
| 2,353,643 | 7/1944 | Bulbulian | 128/207.11 |
| 2,403,046 | 7/1946 | Bulbulian | 128/206.28 |
| 2,998,818 | 9/1961 | Tabor et al. | 128/207.11 |
| 3,752,157 | 8/1973 | Malmin | 128/207.11 |
| 3,776,244 | 12/1973 | Morgan . | |
| 4,149,540 | 4/1979 | Hasslinger . | |
| 4,173,220 | 11/1979 | Ratz et al. . | |
| 4,641,647 | 2/1987 | Behan | 128/207.18 |
| 4,665,566 | 5/1987 | Garrow | 2/171 |
| 4,741,054 | 5/1988 | Mattes | 2/421 |
| 4,766,610 | 8/1988 | Mattes | 2/6 |
| 4,915,106 | 4/1990 | Aulgur et al. | 128/207.11 |
| 5,038,776 | 8/1991 | Harrison et al. | 128/207.11 |
| 5,069,205 | 12/1991 | Urso | 128/201.24 |
| 5,272,772 | 12/1993 | Hahn | 2/195.2 |
| 5,349,949 | 9/1994 | Schegerin | 128/206.24 |

FOREIGN PATENT DOCUMENTS

| | | | |
|---|---|---|---|
| 831819 | 9/1938 | France | 128/207.11 |
| 455973 | 2/1928 | Germany | 128/207.11 |
| 1104122 | 4/1961 | Germany | 128/207.11 |
| 50041 | 3/1941 | Netherlands | 128/207.11 |
| 626927 | 7/1949 | United Kingdom | 128/207.11 |
| 2268388 | 1/1994 | United Kingdom | 2/422 |
| 8907961 | 9/1989 | WIPO | 128/207.11 |

OTHER PUBLICATIONS

Respironics, Inc, "Respironics Sleep Easy Nasal CPAP System", Jan. 30, 1986, pp. 1 and 8.
Respironics, Inc., "Headgear Instructions for Use", Jun. 12, 1990, pp. 1 and 2.
Respironics, Inc., "Softcap Instructions for Use", Jun. 1, 1990, pp. 1 and 2.

Primary Examiner—Kimberly L. Asher
Attorney, Agent, or Firm—Reed Smith Shaw & McClay

[57] ABSTRACT

An adjustable headgear for use with reusable or disposable nasal and/or oral gas delivery masks. The headgear includes a cap-like headpiece adapted to fit the crown and back of a patient's head. Lower strap means provide a two-point connection with the gas delivery mask to achieve a comfortable fit and an effective seal. Depending strap means depending from the head piece are connected to and moveable relative to the lower strap means. The depending strap means offer a stabilizing connection between the head piece and the lower strap means. Upper strap means can be used in the event an effective seal cannot be achieved using only the lower strap means. The upper and lower strap means provide a four-point connection with the gas delivery mask.

10 Claims, 4 Drawing Sheets

TWO-POINT/FOUR-POINT ADJUSTABLE HEADGEAR FOR GAS DELIVERY MASK

BACKGROUND OF THE INVENTION

1. Field of the Invention

This invention relates to adjustable headgear and more particularly to adjustable headgear capable of two-point and four-point connections with a gas delivery mask.

2. Description of the Prior Art

Headgear is known by which a gas delivery mask is maintained in contact with the face of a patient. Such headgear has incorporated upper and lower straps, each having opposite ends threaded through connector elements provided on the opposite sides and the top of a mask. Each strap includes releasable securing means, for example, a Velcro® fastener, such that each strap may be adjusted as required to produce an effective seal between the mask and the patient's face.

Three such headgears are marketed by the assignee of this invention, i.e., RESPIRONICS, INC. One such headgear utilizes a rectangular plastic card adapted to reside on the back of a patients head and to which the upper and lower straps are secured, for example, by means of Velcro® fastener. Such a headgear is described and illustrated, for example, in a brochure entitled "RESPIRONICS SleepEasy® Nasal CPAP System" published by RESPIRONICS, INC., and dated Jan. 30, 1986. The mark "SLEEPEASY" is a trademark of RESPIRONICS, INC.

In a second headgear type, a crown strap spans between the end portions of the upper strap. A back strap is secured at one end to the crown strap and extends therefrom downwardly and interiorly of the upper and lower straps and then upwardly and outwardly of the lower and upper straps to enclose the same. Both the crown strap and the back strap are adjustable to conform the headgear with the shape and size of the patients head. Such a headgear is illustrated, for example, in an instruction sheet for Item No. 302044, entitled "Headgear Instructions for Use" published by RESPIRONICS, INC., and dated Jun. 12, 1990.

In a third headgear type, a hood-shaped cap is provided wherein upper strap segments are attached to the cap so as to be disposed above the ears of the patient; and wherein lower strap segments are attached to the cap along a bottom edge thereof. Such a headgear is illustrated, for example, in an instruction sheet for Item Nos. 302142 and 3022, entitled "Softcap™ Instructions for Use" published by RESPIRONICS, INC., and dated Jun. 1, 1990. The mark "Softcap" is a trademark of RESPIRONICS, INC.

In each of the three headgear examples described above, there is no stabilizing connection between the upper and lower straps. In the third headgear example described above, there is no stabilizing connections between the hood-shaped cap and the lower strap segments.

SUMMARY OF THE INVENTION

The principal object of this invention is to provide a cap-like headgear utilizing a two-point and four-point connections to attach a nasal and/or oral gas delivery mask to a patient's face.

Another object of the invention is to provide a cap-like headgear which is readily adjustable to create an effective seal between the mask and the patient's face.

Still another object of this invention is to provide a cap-like headgear having depending strap means which stabilize the lower strap means thereby assuring a comfortable fit with the head of a patient.

In accordance with this invention, an adjustable headgear is provided comprising a head piece adapted to fit over the crown and back portion of a human head and having upper side edges and lower side edges. Depending strap means are provided, one depending from each of the upper side edges. Lower strap means are provided, one extending from each of the lower side edges, toward one of the depending strap means. Connector means are provided by which each depending strap means is adjustably connected to the adjacent one of the lower strap means, whereby the depending strap means are independently movable along the associated one of the lower strap means to improve the fit of the head piece on the patient's head.

Further, in accordance with the present invention, upper strap means are provided which are connected to the headgear, are disposed above the depending strap means, and terminate in upper connection loops, respectively. The upper strap means are used in the event an effective seal cannot be achieved using only the lower strap means. The upper strap means also is used to adapt the headgear to positive pressure gas delivery masks which require four-point attachment.

These and other objects and advantages of the present invention will become apparent from the following description by reference to the accompanying drawings in which:

DESCRIPTION OF PRESENTLY PREFERRED EMBODIMENT(S)

Figure 1:
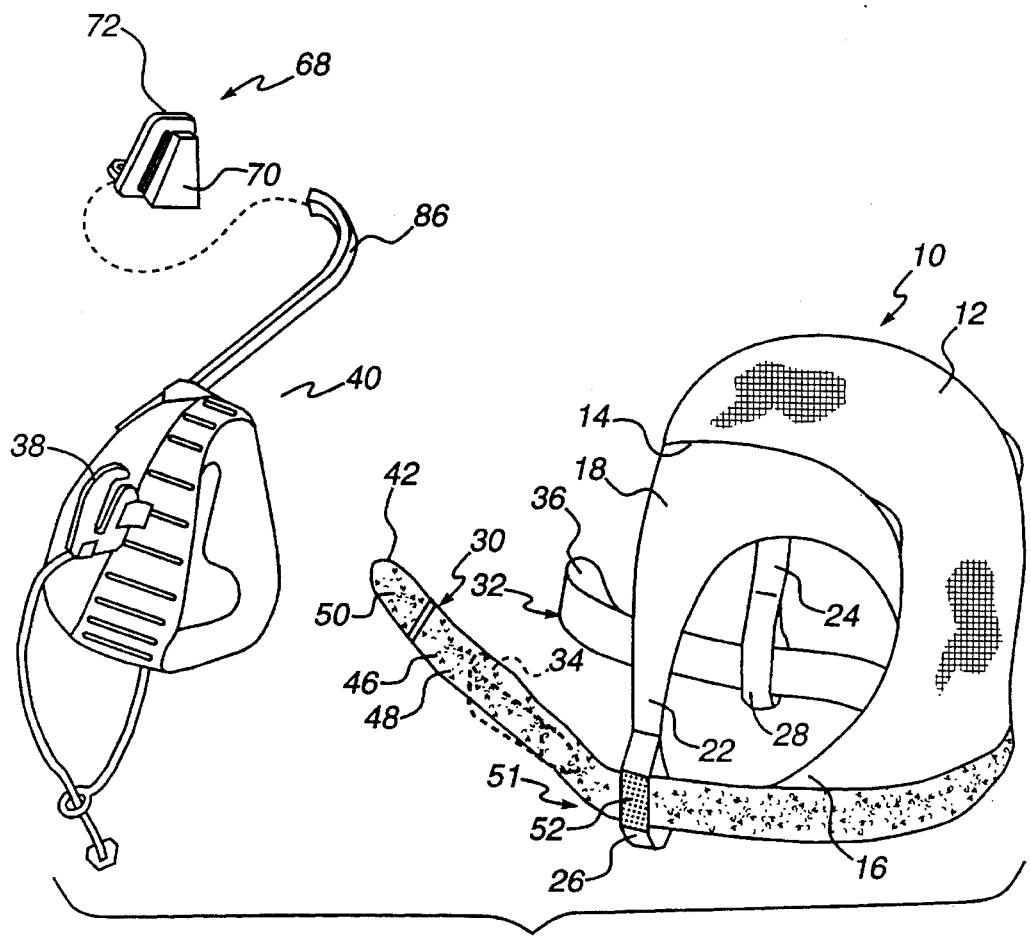
FIG. 1 is an exploded isometric view illustrating adjustable headgear of this invention and an oral/nasal mask.
Figure 3:
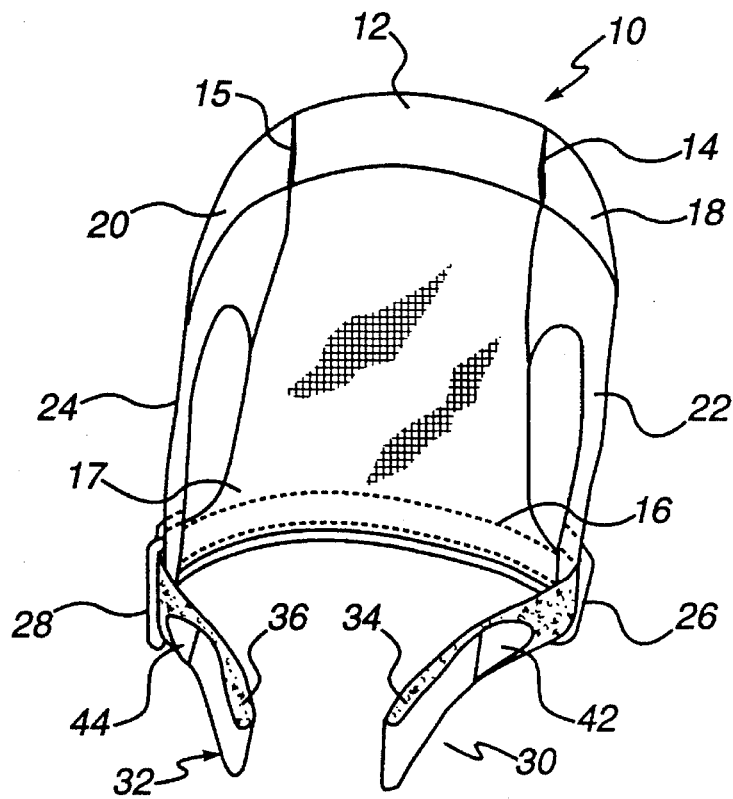
FIG. 3 is a front isometric view of the adjustable headgear of this invention.

Referring to FIGS. 1 and 3, there is illustrated an adjustable headgear 10 of this invention, comprising a head piece 12 having upper side edges 14, 15 positioned along the crown of a patient's head and lower side edges 16, 17 positionable along the back portion of the patient's head. The head piece 12 preferably is formed from net-like material to allow for ventilation of the patient's head. Depending side portion 18, 20 are secured to the upper side edges 14, 15. Depending strap means 22, 24 depend downwardly from the said side portions 18, 20 and terminate in depending strap loops 26, 28, respectively.

The adjustable headgear 10 also includes lower strap means 30, 32 positionable beneath the ears of the patient's head extending towards from the lower side edges 16, 17 and through the depending strap loops 26, 28. The lower strap means 30, 32 terminating in lower connection loops 34, 36 adapting the lower strap means 30, 32 for connection to side connector means 38 (only one visible in FIG. 1) provided on opposite sides of a mask 40. The mask 40 is a nasal/oral mask adapted to enclose the nose and mouth of a patient. Alternatively, the mask 40 may, instead, comprise a nasal mask adapted to enclose only the nose of a patient or an oral mask adapted to enclose only the mouth of a patient.

The lower strap means, 30, 32 include lower strap tabs 42, 44 respectively at the ends thereof. Each of the strap means 30, 32 includes first adjustable securing means for securing the strap tabs 42, 44 at selective locations at the length of the associated one of the strap means 30, 32 to form the lower connecting loops 34, 36. The arrangement is such that the length of the lower connecting loops 34, 36, and hence the length of the lower strap means 30, 32, may be individually adjusted to suit requirements. In the preferred arrangement, the first adjustable securing means includes an adhesive 46 on the exterior face 48 of each of the strap means 30, 32 and cooperating adhesive means 50 on each of the lower strap tabs 42, 44. In the preferred arrangement, the adhesive means 46 and the cooperating adhesive means 50 comprises the two components of a VELCRO® fastener.

As should be apparent in FIG. 1, each of the depending strap loops 26, 28 is movable along the associated lower strap means 30, 32 so as to adjust the fit of the head piece 10 to the patient's head.

Figure 4:
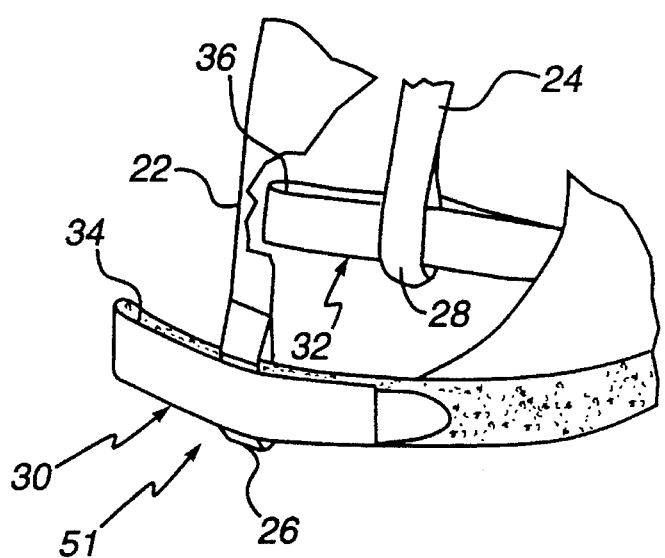
FIG. 4 is a fragmentary isometric view illustrating the lower strap means of the adjustable headgear of this invention.
Figure 5A:
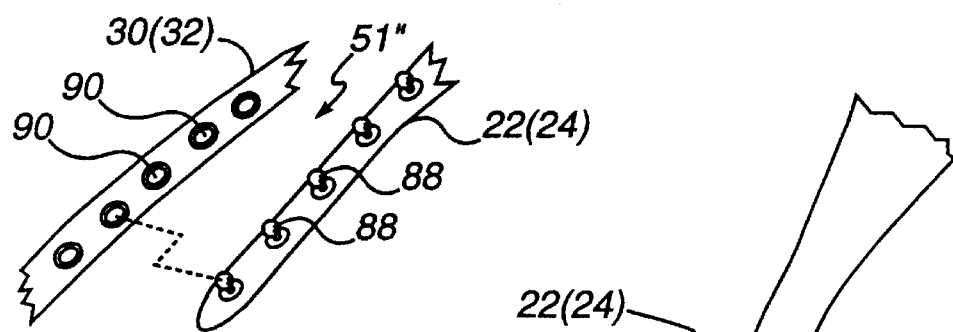
FIG. 5A is a fragmentary isometric view illustrating alternative connector means for adjustably connecting the depending strap means to the lower strap means.
Figure 5:
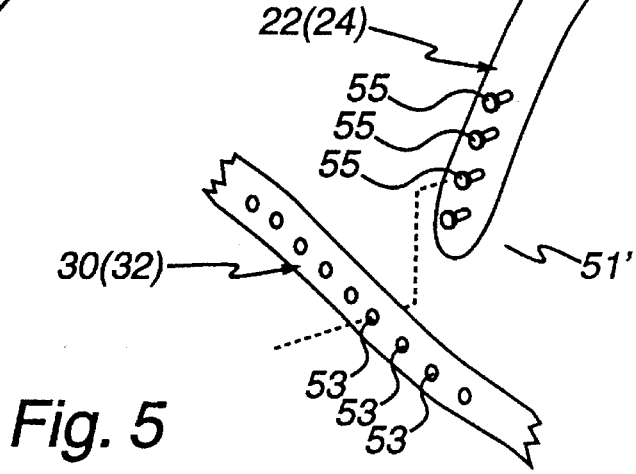
FIG. 5 is a fragmentary isometric view illustrating connector means for adjustably connecting the depending strap means to the lower strap means.

In the preferred arrangement connector means 51 is provided for adjustably connecting each of the depending strap means 22 (24) to an adjacent one of the lower strap means 30 (32). Although by way of example the depending strap means 22, 24 are generally described herein as being adjustable relative to the lower means 30, 32, as will be more fully appreciated from the discussion of FIGS. 5, 5A and 6 below, the adjustability afforded by the connector means 51 may just as validly be viewed from the perspective of the relative adjustability of the lower strap means 30, 32 with respect to the depending strap means 22, 24. Stated differently, by virtue of connector means 51, relative strap adjustment may be effected by moving the depending strap means 22, 24 relative to the lower strap means 30, 32, or vice versa. As shown in FIG. 1, the connector means comprises cooperating adhesive means 52 provided on that face of each of the strap loops 26, 28 facing away from the exterior face 48 of the lower strap means 30, 32; and the adhesive means 46 of the lower strap means 30, 32. As best shown in FIG. 4, one of the strap loops 26, 28 may be captively retained within each of the connecting loops 34, 36. Once the position of the depending strap means 22, 24 is adjusted relative to the lower strap means 30, 32, the cooperating adhesive means 52 (FIG. 1) of the depending strap loops 26, 28 adheres to the adhesive means 46 on the lower strap means 30, 32 thereby immobilizing the depending strap loops 26, 28 relative to the associated one of the lower strap means 30, 32 in the best fit position.

Alternatively, connector means 51' (FIG. 5) may be provided comprising a series of openings 53 along one of the strap means, for example, the lower strap means 30 (32); and at least one and preferably a plurality of pins 55 projecting from an adjacent one of the strap means, for example, the depending strap means 22 (24). One of the pins 55 will be inserted into an appropriate one of the openings 53, the arrangement being such that each of the depending strap means 22, 24 is moveable relative to the associated one of the lower strap means 30, 32 thereby to improve the fit of the head piece on the patient's head.

As a further alternative, connector means 51' (FIG. 5A) may be provided comprising conventional snap fastener means of the type including ball elements 88 disposed, for example, along the depending strap means 22 (24), and complementary socket elements 90 disposed along, for example, the lower strap means 30 (32). One of the ball elements 88 will be inserted into an appropriate one of the socket elements 90, the arrangement being such that each of the depending strap means 22, 24 is moveable relative to the associated one of the lower strap means 30, 32 thereby to improve the fit of the head piece on the patient's head.

Figure 6:
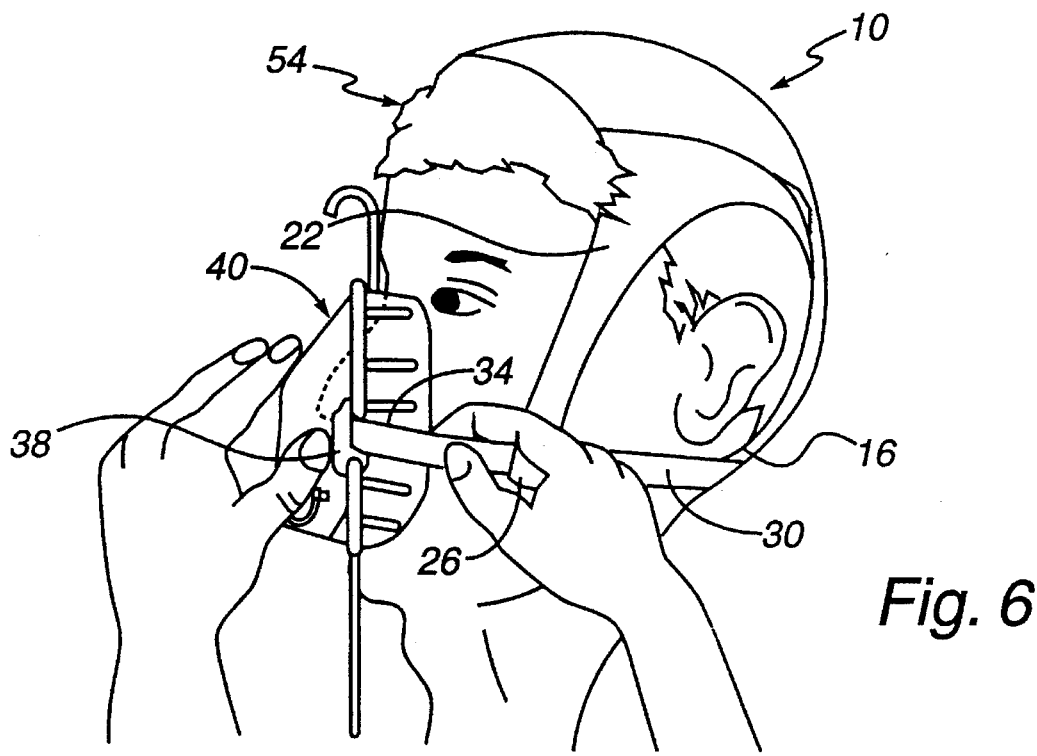
FIG. 6 is a side view of a patient wearing the headgear and mask of FIG. 1.

FIG. 6 illustrates a patient 54 wearing the headgear 10 and the gas delivery mask 40. The lower strap means 30 extends forwardly from the lower head, beneath the patient's ear, and is connected to the side connector 38 of the gas delivery mask 40. Although not visible in FIG. 5, the lower strap means 32 is similarly arranged such that a two-point connection between the headgear 10 and the gas delivery mask 40 is provided. The depending strap means 22 is disposed forwardly of the patient's ear and is connected to the lower strap means 30 by the depending strap loop 26 as explained above. While not visible in FIG. 5, the depending strap means 24 is similarly disposed. Each of the lower strap means 30, 32 is gradually tightened until a comfortable fit exists. Once the mask 40 is connected to a gas source, the lower strap tabs 42, 44, (FIG. 3) of the lower strap means 30, 32 are unhooked and the lower strap means 30,32 are again gradually tightened until an adequate seal and a comfortable fit exists.

Figure 7:
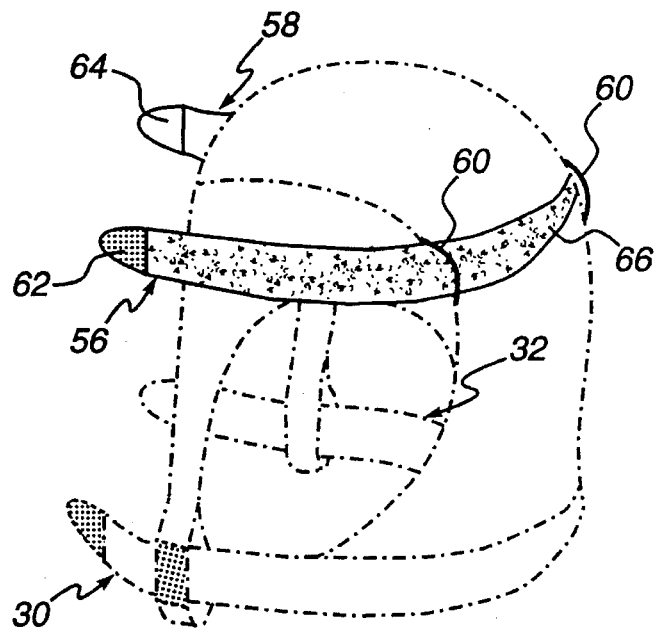
FIG. 7 is an isometric view of an auxiliary strap means providing upper strap means positioned on the present headgear which is shown in dotted outline.

If an adequate seal is not achieved using only the lower strap means 30, 32, upper strap means 56, 58 shown in FIG. 7 may be used. The upper strap means 56, 58 are connected to the headgear, are disposed above the lower strap means 30, 32, and which terminate in upper strap tabs 62, 64, respectively. The upper strap means 56, 58 and the upper strap tabs 62, 64 thereof preferably are provided with the two components of a Velcro® fastener. Thus the upper strap means 56, 58 may each be bent back on itself to adhere the upper strap tabs 62, 64 to the strap means 56, 58. In the preferred arrangement, the upper strap means 56, 58 comprise a single auxiliary upper strap means 66 wherein at least an intermediate portion thereof is detachably connected to the head piece 12 by at least one and preferably two loop means 60 presented by the head piece 12.

Figure 2:
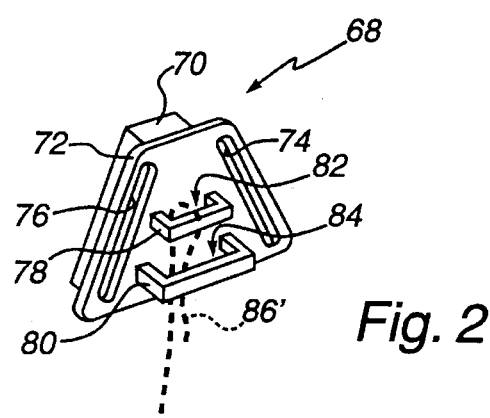
FIG. 2 is an isometric view of a forehead pad assembly.

The upper strap means 56, 58 are used in conjunction with a forehead pad assembly 68 illustrated in FIGS. 1 and 2. The forehead pad assembly 68 comprises a soft pad 70 adapted to engage the forehead of the patient. The pad 70 is secured to a plastic plate 72 which, as best shown in FIG. 2, includes elongated apertures 74, 76 through which the upper strap means 56, 58 are threaded. The plate 72 also includes upper and lower U-shaped members 78, 80 which cooperate with the plate 72 to form an upper opening 82 and larger lower opening 84. The upper and lower openings 82, 84 are adapted to receive a flexible plastic ribbon 86 (FIG. 1) secured to and extending upwardly from the gas delivery mask 40. As shown by the dotted outline 86' in FIG. 2, the ribbon 86 will extend upwardly through the lower opening 84, then upwardly through the upper opening 82 extend outwardly of the U-shaped member 78 and then downward through the lower opening 84. In this manner the forehead pad assembly 60 is connected to the gas delivery mask 40 such that the position of the forehead pad assembly 60 may be adjusted vertically relative to the mask 40.

As in the case of the lower strap means 30, 32, the upper strap means 56, 58 (FIG. 7) and the tab means 62, 64 thereof, include the two components of a Velcro® fastener. Thus, the strap means 56, 58 may be threaded through the elongated apertures 74, 76 (FIG. 2) and then bent back on itself to adhere the tabs 62, 64 to the exterior face of the strap means 56, 58, respectively.

Figure 8:
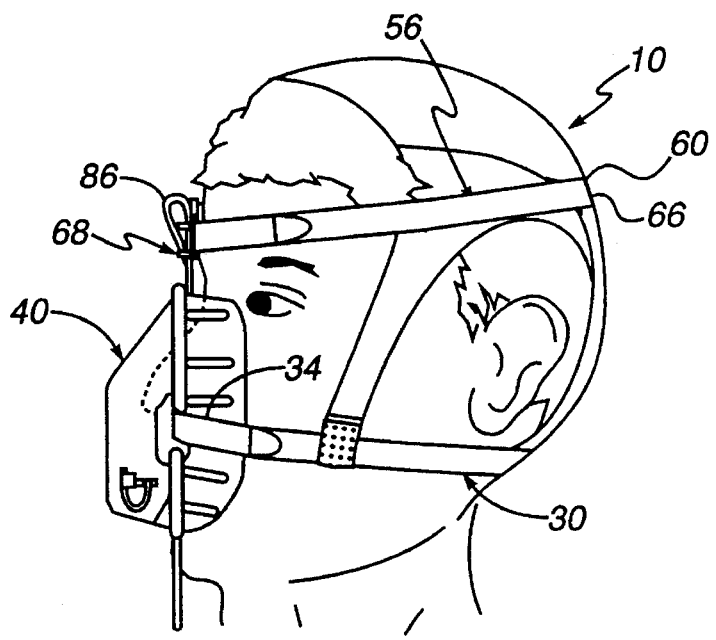
FIG. 8 is a side view of a patient wearing the headgear of FIG. 7.

FIG. 8 illustrates the patient 54 with the upper strap means 56 (58) and the gas delivery mask 40 with the forehead pad assembly 68. As explained above, the ribbon 86 connects the forehead pad assembly 68 to the gas delivery mask 40. The strap means 56 (58) are connected to the forehead pad assembly 68 in the manner explained above. The tabs 62 (64) of the straps 56 (58) are unhooked and the strap means 56 (58) are gradually tightened until a comfortable fit exists and an adequate seal is achieved.

From the foregoing discussion, it should be readily apparent that the present invention provides an adjustable headgear which is capable of a two-point connection with a gas delivery mask to provide a comfortable fit and an effective seal. Should an effective seal not exist with the two-point connection, the present headgear is capable of a four-point connection to improve the seal. It should also be readily apparent that the present adjustable headgear includes depending strap means which stabilize the lower strap means thereby assuring a comfortable fit.

We claim:

1. An adjustable headgear comprising:
   a head piece adapted to fit over the crown and back portion of a human head, said head piece having upper side edges positionable along the crown of a human head and lower side edges positionable along the back portion of a human head;
   a pair of depending straps, one of said pair of said depending straps downwardly depending from each of said upper side edges, each of said depending straps terminating in a depending strap loop;
   a pair of lower straps positionable beneath the ears of a human head, one of said pair of lower straps extending forwardly from each of said lower side edges toward one of said depending straps, said lower straps terminating in lower connection loops, one of each of said depending strap loops being captively retained within one of said lower connection loops and moveable therealong; and
   connector means for adjustably connecting each of said depending straps to an adjacent one of said lower straps, each of said depending loops being movable along the associated one of said lower straps, said connector means further including means for releasably securing each of said depending strap loops to one of said lower connection loops, said means for releasably securing including means provided on each of said depending strap loops for securement to an associated one of said lower connection loops and for immobilizing each of the dependent strap loops relative to an adjacent one of said lower straps, thereby to improve the fit of said head piece on human head.

2. The adjustable headgear as defined in claim 1 wherein said head piece is formed from net-like material.

3. The adjustable headgear as defined in claim 1 further comprising at least one upper strap connected to said head piece, said at least one upper strap being disposed above said lower straps and terminating in at least one connection loop.

4. The adjustable headgear as defined in claim 3 further comprising:
   at least one loop provided on said head piece; and
   said at least one upper strap comprises a single axially strap,
      whereby said at least one loop on said head piece detachably connects at least an intermediate portion of said single auxiliary strap to said head piece.

5. A patient gas delivery system comprising:
   a mask adapted to fit over the face of a patient and having first connector means on opposite sides thereof for connecting said mask to a head piece adapted to fit over the crown and back portion of a patient's head, said head piece comprising:
   upper side edges positionable along the crown of a patient's head and lower side edges positionable along the back portion of a patient's head;
   a pair of depending straps, one of said pair of depending straps downwardly depending from each of said upper side edges, each of said depending straps terminating in a depending strap loop;
   a pair of lower straps positionable beneath the ears of a patient's head, one of said pair of lower straps extending forwardly from each of said lower side edges toward one of said depending straps, said lower straps terminating in lower connection loops, one of each of said depending strap loops being captively retained within one of said lower connection loops and moveable therealong, each of said lower connection loops being connected to said first connector means thereby providing two-point connection with said mask; and
   second connector means for adjustably connecting each of said depending straps to an adjacent one of said lower straps, each of said depending loops being moveable along the associated one of said lower straps, said second connector means further including means for releasably securing each of said depending strap loops to one of said lower connection loops, said means for releasably securing including means provided on each of said depending strap loops for securement to an associated one of said lower connection loops and for immobilizing each of the dependent strap loops relative to an adjacent one of said lower straps, thereby to improve the fit of said head piece on a patient's head.

6. The patient gas delivery system as defined in claim 5 further comprising:
   at least one upper strap connected to said head piece above said depending straps; and
   third connected means at the top of said mask for connecting said mask to said head piece,
      wherein said at least one upper strap terminates in at least one upper connection loop and is connected to said third connector means.

7. The patient gas delivery system as defined in claim 6 further comprising:
   a least one loop provided on said head piece; and
   said at least one upper strap comprises a single auxiliary strap,
      whereby said at least one loop on said head piece detachably connects at least an intermediate portion of said single auxiliary strap to said head piece.

8. The patient gas delivery system as defined in claim 5 wherein said mask comprises an oral gas delivery mask.

9. The patient gas delivery system as defined in claim 5 wherein said mask comprises a nasal gas delivery mask.

10. The patient gas delivery system as defined in claim 5 wherein said mask comprises an oral/nasal gas delivery mask.

* * * * *

UNITED STATES PATENT AND TRADEMARK OFFICE
CERTIFICATE OF CORRECTION

PATENT NO. : 5,517,986
DATED : May 21, 1996
INVENTOR(S) : Starr et al.

It is certified that error appears in the above-indentified patent and that said Letters Patent is hereby corrected as shown below:

Column 6, line 2 (i.e. line 4 of Claim 4),
"axially" should read --auxiliary--.

Column 6, line 47 (i.e. line 5 of Claim 6),
"connected" should read --connector--.

Signed and Sealed this

Eighteenth Day of August, 1998

Attest:

BRUCE LEHMAN

Attesting Officer         Commissioner of Patents and Trademarks